(12) United States Patent
Dalmases Barjoan et al.

(10) Patent No.: US 7,728,021 B2
(45) Date of Patent: Jun. 1, 2010

(54) PROCESS FOR THE PREPARATION OF VALSARTAN AND PRECURSORS THEREOF

(75) Inventors: Pere Dalmases Barjoan, Sant Feliu de Llobregat (ES); Jordi Bessa Belmunt, Barcelona (ES); Joan Huguet Clotet, Sant Joan Despi (ES); Juan Antonio Perez Andres, Sant Joan Despi (ES)

(73) Assignee: INKE, S.A., Castellbisbal (ES)

( * ) Notice: Subject to any disclaimer, the term of this patent is extended or adjusted under 35 U.S.C. 154(b) by 862 days.

(21) Appl. No.: 11/568,054

(22) PCT Filed: Apr. 18, 2005

(86) PCT No.: PCT/IB2005/001100

§ 371 (c)(1),
(2), (4) Date: Oct. 18, 2006

(87) PCT Pub. No.: WO2005/102987

PCT Pub. Date: Nov. 3, 2005

(65) Prior Publication Data

US 2009/0221836 A1 Sep. 3, 2009

(30) Foreign Application Priority Data

Apr. 20, 2004 (ES) ................. 200400949

(51) Int. Cl.
*A61K 31/41* (2006.01)
*C07D 257/00* (2006.01)
(52) U.S. Cl. ...................... 514/381; 548/250
(58) Field of Classification Search ................. 514/381; 548/250
See application file for complete search history.

(56) References Cited

U.S. PATENT DOCUMENTS 5,596,006 A * 1/1997 Dressel et al. ............... 514/340
5,965,592 A * 10/1999 Buhlmayer et al. ......... 514/381

FOREIGN PATENT DOCUMENTS

| DE | 43 13 747 A1 | 11/1994 |
| DE | 44 07 488 A1 | 9/1995 |
| EP | 0 443 983 A1 | 8/1991 |
| EP | 0 594 022 A1 | 4/1994 |
| WO | WO 96/09301 | 3/1996 |
| WO | WO 03/020721 A1 | 3/2003 |

OTHER PUBLICATIONS

Oehberg L. et al.: "One-pot Three-step Solution Phase Synthesis of Thiohydantoins Using Microwave . . . ". SYNLETT, vol. 12, 2001, pp. 1893-1896, XP001207553 table 2; compound 7.

Moenius T. et al.: "Carbon-14 Labelling of . . . ". Journal of Labelled Compounds and Radiopharmaceuticals, Sussex, GB, vol. 43, 2000, pp. 1245-1252, XP002292105 ISSN: 0362-4803.

* cited by examiner

Primary Examiner—Susannah Chung
(74) Attorney, Agent, or Firm—Cozen O'Connor

(57) ABSTRACT

This invention relates to a process for preparing intermediates useful in preparing Valsartan and to a process for preparing the latter, together with synthesis intermediates of formula (IV), (V) and (VI), useful for manufacturing a medicament for the treatment of arterial hypertension or heart failure. The process for preparing Valsartan permits it to be prepared on an industrial scale with high yields and without racemisation problems, in addition to using simple and available starting products. The invention also provides a process for preparing the intermediate of formula (VI), from an intermediate of formula (V) that does not require protection of the carboxylic acid prior to N-acylation.

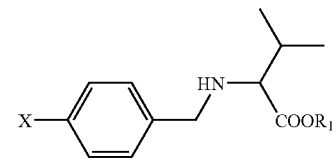

IV

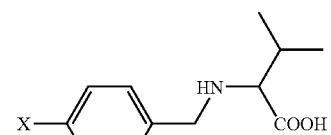

V

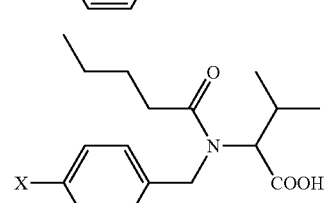

VI

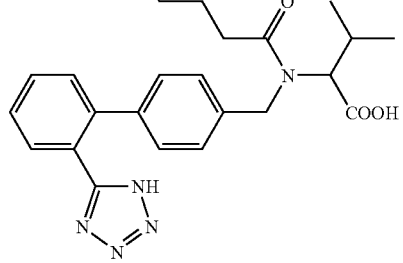

I

10 Claims, No Drawings

PROCESS FOR THE PREPARATION OF VALSARTAN AND PRECURSORS THEREOF

FIELD OF THE INVENTION

This invention relates to a process for preparing intermediates useful for making a pharmaceutically active compound for manufacturing a medicament for treating arterial hypertension or heart failure, and to a process for preparing said pharmaceutically active compound.

In particular, this invention relates to a process for preparing Valsartan, its synthesis intermediates and to the processes for preparing said intermediates.

BACKGROUND OF THE INVENTION

Spanish patent ES 2084801T (equivalent to European patent EP 443983) discloses acyl compounds, among them the Valsartan of formula (I):

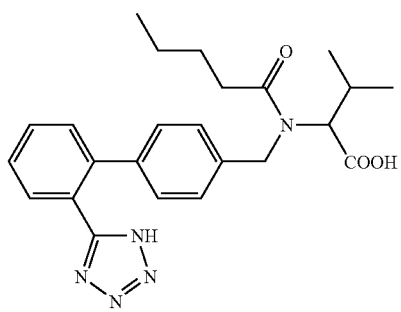

I

Said Spanish patent discloses how it is prepared by converting a phenyl substituent ($Z_1$) into tetrazole, where $Z_1$ is a group convertible into tetrazole, and can among others be a halogen group. The examples of said patent describe the specific case in which $Z_1$ is a cyano group or a protected tetrazole ring. This is followed by final deprotection of the carboxylic acid group, where R is preferably methyl or benzyl and, where applicable, of the tetrazole ring protective group, preferably a trityl group.

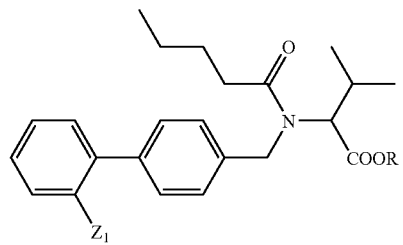

That patent, leaves room for improvement of aspects such as the utilisation of azide in the last synthesis steps, with the attendant risk of explosion if sodium azide is used or environmental problems if tributyl tin azide is used.

Another negative aspect lies in the use of large protective groups for both the tetrazole ring (trityl group) and for the carboxylic acid of the valine moiety (benzyl group), which increase very considerably the molecular weight, of the last synthesis intermediate, which is dramatically reduced subsequently in the final hydrolysis to yield Valsartan, resulting in a process of low atomic efficiency. This further creates a considerable amount of residual products and increases the number of synthesis steps in the process.

Patents DE4313747, DE4407488, U.S. Pat. No. 5,596,006, EP594022 and WO9609301 describe the synthesis of sartans by means of formation of the biphenyl system by reacting an aryl halide with the 2-(1H-tetrazol-5-yl) phenylboronic acid in the presence of a palladium catalyst.

A safe, ecological and high-yield process for obtaining Valsartan with few synthesis steps and using simple and commercially available starting products therefore remains necessary. Additionally, it must be possible to apply said process on an industrial scale and avoiding racemisation and the consequent separation of enantiomers.

DESCRIPTION OF THE INVENTION

A first aspect of this invention is therefore to provide a process for preparing Valsartan that permits it to be obtained with high yields. Surprisingly, with the process defined in accordance with the first aspect of the invention, Valsartan is obtained without racemisation problems. In particular, the last synthesis intermediate of formula (VI) can be obtained with an enantiomeric excess (e.e.) of 100%.

Also advantageously, the process for preparing Valsartan defined in claim 1 uses simple and available starting products that avoid the formation of tetrazole, as the latter is already incorporated into the starting product and there is therefore no need to work, with sodium azide in the last synthesis steps, thereby avoiding safety problems in preparing it.

It is furthermore a very clean process from the environmental point, of view, as the penultimate synthesis step does not involve the use of tributyl tin azide, which produces large amounts of a toxic by-product, or hexabutyl ditannic oxane, with the attendant, problems of treating residues of this type.

More advantageously still, the process defined in a first aspect of the invention does not use protective groups of tetrazole or of the carboxylic acid group of the valine moiety of the last synthesis intermediate VI. This, together with the fact that the last synthesis step is a catalytic reaction, favours what is understood as the atomic efficiency of the process, that is, the proportion of atoms of the respective starting reagents that are incorporated into the desired product is optimum and translates into a considerable reduction of the amounts of residues to be treated.

In accordance with the process according to the first aspect of the invention, Valsartan can be obtained with few synthesis steps; in particular, only three steps are necessary if silylating agents are used.

A second aspect of the invention is the synthesis intermediate defined by formula (IV).

A third aspect of the invention is the synthesis intermediate defined by formula (V).

A fourth aspect of the invention is the synthesis intermediate defined by formula (VI).

A fifth aspect of the invention is to provide another process for preparing the synthesis intermediate of formula (V).

A sixth aspect of the invention is to provide a process for preparing the synthesis intermediate of formula (VI).

A seventh aspect of the invention is to provide a process for preparing Valsartan by coupling the advanced intermediate of formula VI with the compound of formula VII. Said process manages to prevent racemisation and is therefore very useful for preparing Valsartan on a large industrial scale.

Definitions

In this invention, the term "carboxylic acid protective groups" is taken to mean any protective group of carboxylic acids of the optionally substituted methyl, ethyl or silyl ester type, described in "Protective groups in organic synthesis", T. W. Greene, P. G. M. Wats 3ª Ed. (1999), page 369. Methyl, ethyl or methylsilyl groups are preferably chosen from among the protective groups described.

The term "leaving group" is taken to mean any group that can be displaced by the amine group in intermediates III and VIII. Among the leaving groups described, the preferable choice is halogen, especially bromine or —$OSO_2R$, where R is $CF_3$, tolyl, methyl or F.

The term "organic base" is taken to mean a substituted amine type compound. Preferably, the latter is chosen from trialkylamine, especially diisopropylethylamine (DIPEA).

The term "aprotic organic solvent" is taken to mean a solvent that is not capable of exchanging protons with the reagents. Preferably, said aprotic organic solvent is chosen form tetrahydrofuran (THF) or dimethylformamide (DMF), according to the stage of the process.

The term "palladium catalyst" is taken to mean a palladium compound, which can be homogeneous and soluble in the reaction medium, such as $Pd(PPh_3)_4$, $PdCl_2$ $(PPh_3)_2$, $Pd(AcO)_2$/or heterogeneous and insoluble in the reaction medium, such as Pd/C.

The term "ligand" is taken to mean a phosphine or carbene type compound. Preferably, said ligand is a triarylphosphine type.

The term "work up" is taken to mean the subsequent work of isolation and/or purification following the reaction, in which extractions or precipitations can take place in an aqueous medium.

The terra "one pot" is taken to mean a series of consecutive reactions which are carried out without isolating the respective intermediates.

DETAILED DESCRIPTION OF THE INVENTION

This invention has the object of providing a new process for preparing Valsartan of formula (I), which permits it to be obtained with good yields and does not present problematic safety or environmental aspects.

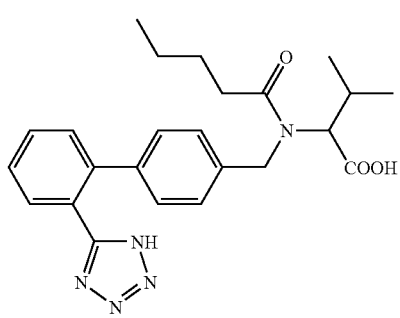

I

The process for preparing Valsartan in accordance with the first aspect of the invention is characterised in that it includes the following stages (Scheme I):

a) Displacement of the Y group of a compound of formula (II) by the protected L-valine of formula (III):

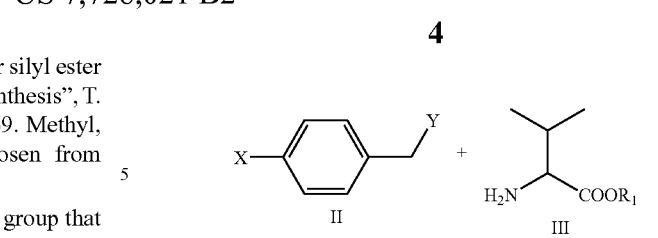

where:

X means halogen or an —$OSO_2R$ group, in which R is $CF_3$, tolyl, methyl or F;

Y means any leaving group that can be displaced by the amine of the compound of formula (III); and $R_1$ means a protective group of carboxylic acids, at a temperature between 25° C. and 150° C., preferably between 40 and 100° C., and in the presence of an aprotic organic solvent, preferably dimethylformamide (DMF), and an organic base, preferably a trialkylamine, more preferably DIPEA, or an inorganic base, preferably an inorganic base capable of picking up the HY acid given off in the substitution, to give a compound of formula (IV):

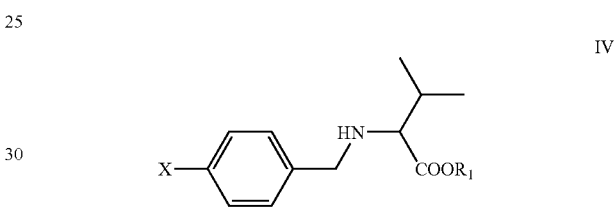

where X and $R_1$ have the meanings defined above, as long as when X is Cl, $R_1$ is other than methyl;

b) Deprotection of the $R_1$ group of the compound of formula (IV), preferably by means of hydrolysis in an acid or basic medium, in order to give the compound of formula (V):

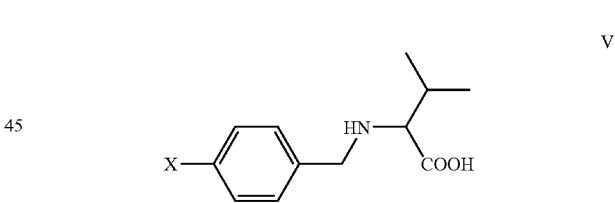

c) N-acylation of the compound of formula (V) with valeroyl chloride in an aprotic organic solvent medium, preferably tetrahydrofuran (THF), in the presence of an organic or inorganic base, preferably $NaHCO_3$/and at a temperature ranging between −20 and 40° C., preferably between −10 and 10° C., to give the compound of formula. (VI):

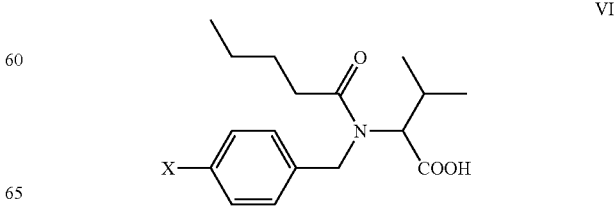

d) Coupling of the compound of formula (VI) with the 2-(1H-tetrazol-5-yl)phenylboronic acid (obtained in accordance with the process described in patent DE 4313737), of formula (VII):

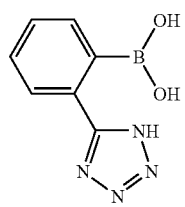

VII in a solvent medium chosen from aqueous or polar organic, or a mixture of water and water-miscible solvent, in the presence of an organic or inorganic base, capable of forming a salt with the tetrazole ring of the compound of formula (VII), at a temperature ranging between 25 and 150° C., with a palladium catalyst and, if so required, a ligand, in order to provide Valsartan of formula (I) and eventually, if necessary, a pharmaceutically acceptable salt thereof.

Scheme I shows the complete sequence of stages:

SCHEME I

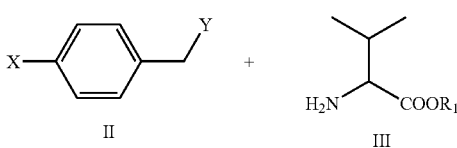

II  III

↓ a

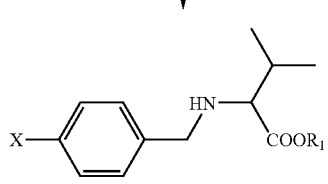

IV

↓ b

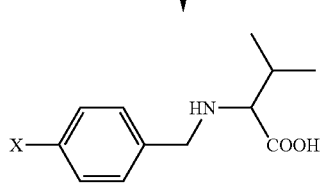

V

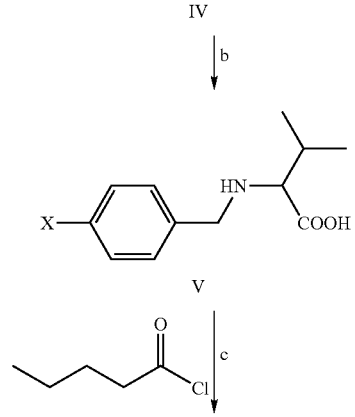

↓ c

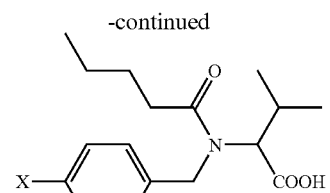

VI

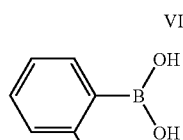

VII

↓ d

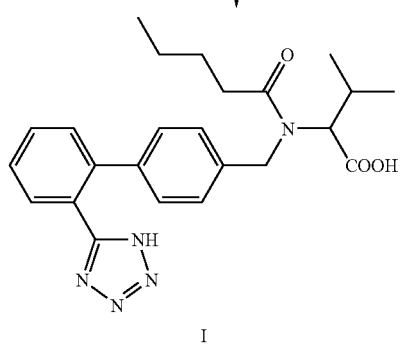

I

A second aspect of the invention is the synthesis intermediate of formula (IV):

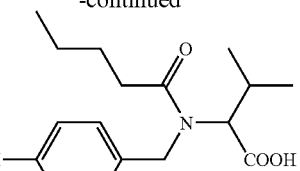

IV where X means halogen or an —OSO$_2$R group, where R is CF$_3$, tolyl, methyl or F, and R$_1$ a protective group of carboxylic acids, as long as when X is Cl, R$_1$ is other than methyl.

A third aspect of the invention is the synthesis intermediate of formula (V):

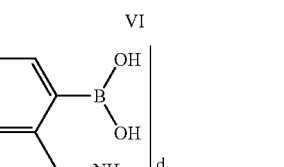

V where X means halogen or an —OSO$_2$R group, where R is CF$_3$, tolyl, methyl or F.

A fourth aspect of the invention is the synthesis intermediate of formula (VI):

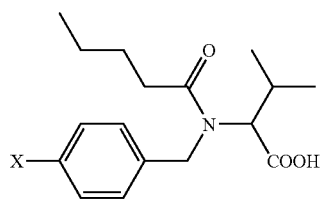

where X means halogen or an —OSO$_2$R group, where R is CF$_3$, tolyl, methyl or F.

A fifth aspect of the invention is to provide an alternative process for preparing the synthesis intermediate of formula (V), which is characterised in that it includes:

a) Displacement of the Y group of a compound of formula (II) by the L-valine protected by trimethylsilyl groups (TMS) of formula (VIII):

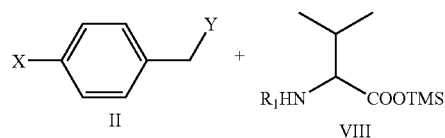

where:

X means halogen or an —OSO$_2$R group, where R is CF$_3$, tolyl, methyl or F;

Y means any leaving group capable of being displaced by the amine of the compound VIII; and R$_1$ means hydrogen or a trimethylsilyl (TMS) group, at a temperature of between 25° C. and 150° C. and in the presence of an aprotic organic solvent and an organic or inorganic base capable of taking up the HY acid given off in the substitution, to give a compound of formula (IX):

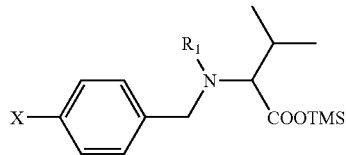

where X and R$_1$ have the meanings defined above, followed by:

b) Deprotection of the TMS groups of the compound of formula (IX) in an aqueous "work-up", to give finally the compound of formula (V):

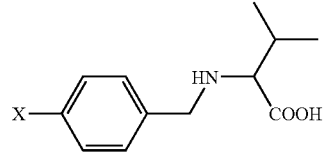

Advantageously, said stages a) and b) are carried out in a "one pot" reaction. This process occurs differently according to the silylating agent chosen.

Thus, where the silylating agent is 1,1,1,3,3,3-hexamethyldisilazane (HMDS), said "one pot" reaction includes (Scheme II):

a) Prior formation of the p-toluenesulphonate of the L-valine in a polar solvent;

b) "In situ" protection of the p-toluenesulphonate of the L-valine with one equivalent, of 1,1,1,3,3,3-hexamethyldisilazane (HMDS) (A. Arrieta; Syn. Commun. 1050-52 (1982)) in the presence of an aprotic organic solvent under anhydrous conditions;

c) Displacement of the Y group of the compound of formula (II) at a temperature of between 25 and 150° C. and in the presence of an organic base; and d) Hydrolysis of the trimethylsilyl groups in an aqueous "work-up", to give the compound of formula (V).

Scheme II below shows the complete sequence of stages:

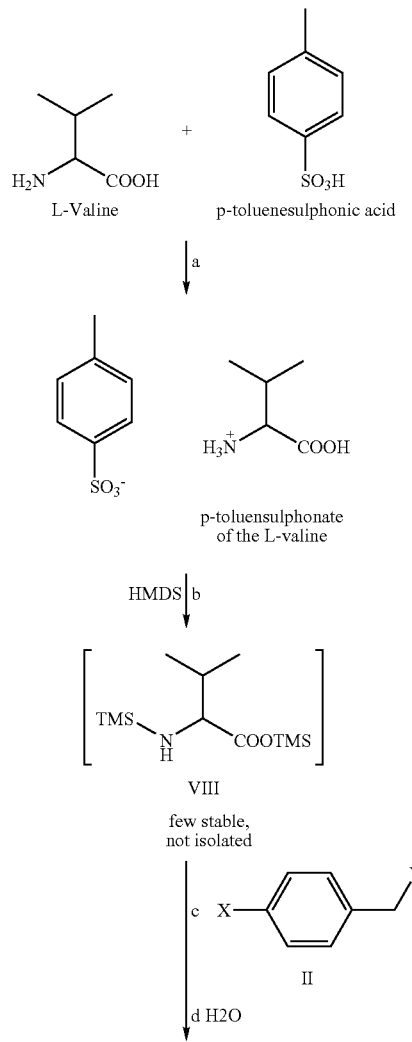

-continued

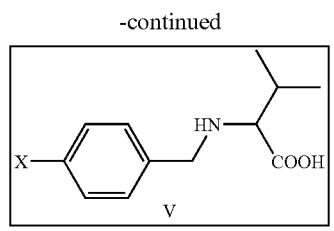

V

In said synthesis, in step a) formation of the p-toluenesulphonate of the L-valine is carried out in a polar solvent, preferably alcohol or water. In step b) the reaction takes place with 1 equivalent of 1,1,1,3,3,3-hexamethyldisilazane in an aprotic organic solvent, under anhydrous conditions, to provide a few stable silylated compound that is not isolated. In step c) the same aprotic organic solvent is used as in step b), at a temperature of between 25° C. and 150° C., preferably between 40° C. and 100° C., and in the presence of an organic base of the trialkylamine type, preferably DIPEA. And finally, in step d) hydrolysis of the trimethylsilyl groups takes place in an aqueous "work-up".

Moreover, when N,O-bis(trimethylsilyl)acetamide (BSA) is chosen as silylating agent, said "one pot" reaction comprises (Scheme III):

a) "In situ" protection of the carboxylic acid of the L-valine with 1 equivalent of N,O-Bis(trimethylsilyl)-acetamide (BSA) (J. F. Klebe; J. Am. Chem. Soc. 88, 3390-95 (1966) in the presence of an aprotic organic solvent under anhydrous conditions.

b) Displacement of the Y group of the compound of formula (II) at a temperature of between 25 and 150° C. and in the presence of an organic base;

c) Hydrolysis of the trimethylsilyl group in an aqueous "work-up" to give the compound of formula (V).

Scheme III below shows the complete sequence of stages:

SCHEME III Shynthesis "one pot" with BSA

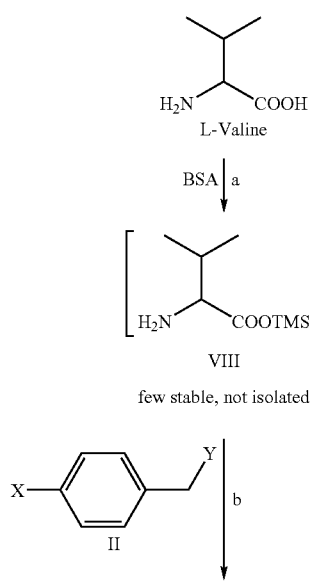

-continued

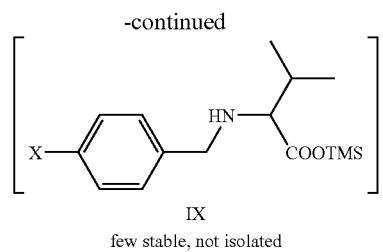

IX
few stable, not isolated

H₂O | c

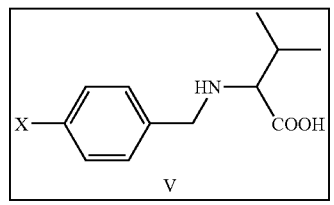

V

In said synthesis, in step a) the reaction of the L-valine takes place with 1 equivalent of N,O-Bis (trimethyl-silyl) acetamide in an aprotic organic solvent, preferably DMF, under anhydrous conditions. In step b) the same aprotic organic solvent is used as in step a), at a temperature of between 25° C. and 150° C., preferably between 40° C. and 100° C., and in the presence of an organic base of the trialkylamine type, preferably DIPEA. And finally, in step c) hydrolysis of the trimethylsilyl group takes place in a neutral to acid aqueous medium.

A sixth aspect of the invention is to provide a process for preparing the synthesis intermediate of formula (VI), characterised in that in consists in N-acylation, without protection of the carboxylic acid of the compound of formula (V), with valeroyl chloride:

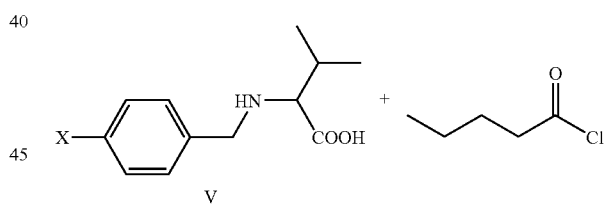

V in the presence of an aprotic organic solvent and an organic or inorganic base and at a temperature of between −20 and 40° C., to give the compound of formula (VI):

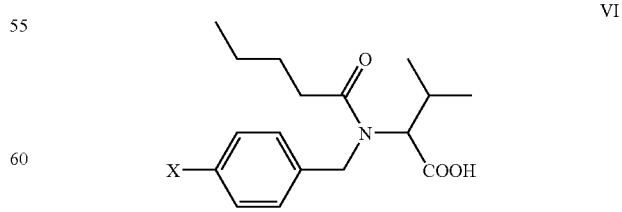

VI

Advantageously, said aprotic organic solvent is tetrahydrofuran (THF) and said inorganic base is NaHCO₃.

Also advantageously, said acylation is carried out at a temperature of between −10 and 10° C.

With the process according to the sixth aspect of the invention the compound of formula (VI) is achieved with good yields and in few reaction steps [2 steps when the "one pot" reaction is effected in order to obtain the compound of formula (V)] from simple and commercially available raw materials.

Surprisingly and unexpectedly, the invention provides a process for preparing the compound of formula (VI) without racemisation, from a compound of formula (V) that does not require protection of the carboxylic acid prior to M-acylation, in which case the final deprotection by means of acid or base hydrolysis provides a product of formula (VI) with 20-35% of undesirable racemisation.

Advantageously, the compound of formula (VI) is obtained with an optical purity of 99.5-100%, which eventually allows very good quantities of Valsartan to be obtained, and therefore greatly simplifies the subsequent process of purification of said active substance.

A seventh aspect of the invention is to provide a process for preparing Valsartan, of formula I, by coupling the intermediate of formula VI with the compound of formula VII:

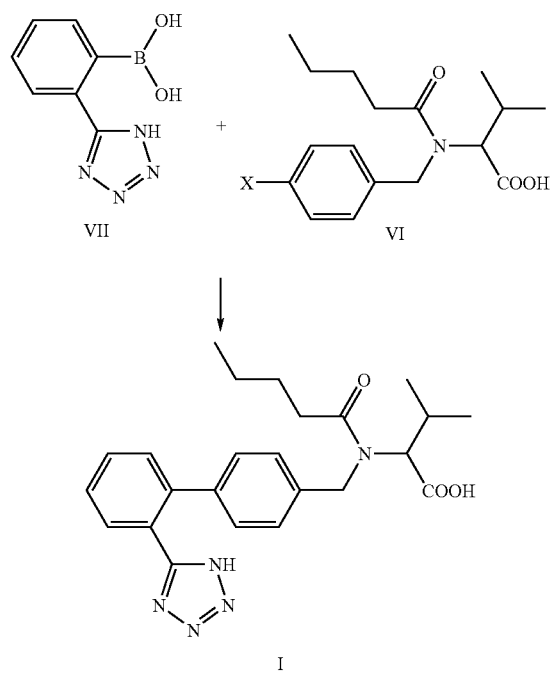

Advantageously, this coupling takes place without need to use protective groups either for the tetrazole ring of the compound of formula VII or for the carboxylic acid group of the intermediate of formula VI. The reaction is effected in the presence of an organic or inorganic base able to form a salt with the tetrazole ring and in the presence of catalytic amounts of a palladium compound. The reaction can be carried out in a polar or aqueous inorganic solvent, or a mixture of water and a water-miscible solvent at a temperature of between 25° C. and 150° C., preferably between 50° C. and 100° C. This coupling can be effected in homogeneous phase, if the palladium compound is soluble in the reaction medium, as is the case of Pd(PPh$_3$)$_4$, PdCl$_2$ (PPh$_3$)$_2$, Pd(AcO)$_2$, or in heterogeneous phase if the palladium compound is insoluble in the reaction medium, as in the case of Pd/C. If Pd/C is used, the coupling reaction requires the presence of catalytic amounts of a ligand, preferably of the phosphine type, especially triphenylphosphine or a water-soluble phosphine such as the trisodium salt of 3,3', 3"-phosphinidinatris (benzenesulphonate). The latter has the advantage of allowing the reaction to be carried out using water as solvent.

In this invention Valsartan is advantageously obtained with good chemical yield and high optical purity, by means of a process applicable on an industrial, scale and starting from simple and commercially available products through synthesis intermediates that do not require protection of the tetrazole ring or of the carboxylic acid of the L-valine moiety, nor the use of sodium azide or tributyl tannic azide, with consequent improvement in the safety of the process and respect for the environment.

There follow some examples which show non-restrictively some preferred embodiments of the various aspects thereof.

EXAMPLES

Example 1

Obtaining the methyl ester of N-(4-bromobenzyl)-L-valine

A mixture made up of 5 g (20 mmol) 4-bromobenzylo bromide, 4.02 g (24 mmol) methyl ester hydrochloride of the L-valine and 7.7 mL (44.2 mmol) of diisopropylethylamine in 4.75 mL of dimethylformamide is heated to 90° C. After 1 h at 90° C. the mixture is cooled to 20-25° C., 20 mL of toluene is added and it is washed twice with 10 mL of water. The organic phase is dried with anhydrous sodium sulphate and concentrated in vacuo to dryness to provide 5.7 g (95%) of the methyl ester of N-(4-bromobenzyl)-L-valine in the form of an oil.

IR (film, cm$^{-1}$): 3350, 2980, 1740, 1490, 1200, 1180, 1150, 1010.

NMR $^1$H (CDCl$_3$), δ (ppm): 0.93 (dd, 6H, —CH(CH$_3$)$_2$), 1.8-2.0 (m, 1H, —CH(CH$_3$)$_2$), 2.95 (d, 1H, —CH—COOCH$_3$), 3.4-3.9 (dd, 2H, Ar—CH$_2$—), 3.75 (s, 3H, —COOCH$_3$), 7.25 (d, 2 Hr ArH), 7.45 (d, 2H, ArH).

Example 2

Obtaining the methyl ester of the N-(4-iodobenzyl)-L-valine

In a similar way to that of example 1, 2.3 g (98.3%) of the methyl ester of N-(4-iodobenzyl)-L-valine is prepared from 2 g (6.74 mmol) of 4-iodobenzylo bromide.

IR (film, cm$^{-1}$): 3330, 2980, 1740, 1480, 1200, 1130, 1150, 1010.

NMR $^1$H (CDCl$_3$), δ (ppm): 0.93 (dd, 6H, —CH(CH$_3$)$_2$), 1.8-2.0 (m, 1H, —CH(CH$_3$)$_2$), 2.95 (d, 1H, —CH—COOCH$_3$), 3.4-3.9 (dd, 2H, Ar—CH$_2$—), 3.7 (s, 3H, —COOCH$_3$), 7.1 (d, 2H, ArH), 7.6 (d, 2H, ArH).

Example 3

Obtaining N-(4-bromobenzyl)-L-valine (1) A mixture made up of 1.34 g (4.45 mmol) of the methyl ester of N-(4-bromobenzyl)-L-valine obtained in example 1 and 0.62 g (9.39 mmol) of 85% KOH dissolved in 15 μL of methanol and 1 mL of water is heated at reflux. After maintaining the reaction for 3 h at reflux, it is cooled to 20-25° C. and acidified to pH 4-5 with HCl 1N. After stirring the suspension for 1 h at 20-25° C., it is filtered and washed with water to provide 1 g (78.3%) of N-(4-bromobenzyl)-L-valine. M.p.=239-241° C.

The enantiomeric purity is determined by chiral HPLC, giving e.e.=98.56%

IR (KBr, cm$^{-1}$): 2950, 1610, 1490, 1470, 1390, 1210, 1030, 840.

NMR $^1$H (D$_2$O), sodium salt of N-(4-bromobenzyl)-L-valine, δ (ppm): 0.90 (t, 6H, —CH(C$\underline{H}_3$)$_2$), 1.7-1.9 (m, 1H, —C$\underline{H}$(CH$_3$)$_2$), 2.83 (d, 1H, —C$\underline{H}$—COONa), 3.4-3.8 (dd, 2H, Ar—C$\underline{H}_2$—), 7.27 (d, 2H, ArH), 7.55 (d, 2H, ArH).

(2) To a suspension of 10 g (34.6 mmol) of p-toluenesulphonate of L-valine in 100 mL of CH$_2$Cl$_2$ is added at 20-25° C. and under nitrogen atmosphere 8.0 mL (38 mmol) of 1,1,1,3,3,3-hexamethyldisilazane. After shaking the mixture at 20-25° C. for one hour, 13.2 mL (76 mmol) of diisopropylethylamine and 8.64 g (34.6 mmol) of 4-bromobenzylo bromide are added and heated at reflux. When all the 4-bromobenzylo bromide has been consumed, the solvent is evaporated off at low pressure, 100 mL of water is added and after 1 h at 0° C. the solid is filtered and dried in an air oven at 40° C. to provide 8.8 g (89%) of N-(4-bromobenzyl)-L-valine.

The enantiomeric purity is determined by chiral HPLC, giving e.e.=100%

(3) 52 mL (0.21 mol) of N,O-bistrimethylsilylacetamide is added under nitrogen atmosphere to a mixture made up of 23.5 g (0.20 mol) of L-valine and 38.5 mL (0.22 mol) of diisopropylethylamine in 12.5 mL of DMF. After 1 h at 80° C. the suspension changes to a clear solution. Then, in portions and controlling exothermy, 50 g (0.20 mol) of 4-bromobenzylo bromide is added and left to react at 80° C. for 2 h. The mixture is cooled to 20-25° C., 250 mL of toluene and a solution made up of 250 mL of water and 80 mL of NaOH 40% are added. The resulting aqueous phase is washed twice with 100 mL of AcOEt, the remains of solvent distilled and taken to pH 6-7 with HCl 3N. The solid obtained is filtered with 250 mL of IPA to give 43.9 g (76.5%) of N-(4-bromobenzyl)-L-valine.

The enantiomeric purity is determined by chiral HPLC, giving e.e.=100%

Example 4

Obtaining N-(4-iodobenzyl)-L-valine (1) A mixture made up of 2.3 g (6.62 mmol) of the methyl ester of N-(4-iodobenzyl)-L-valine obtained in example 2 and 0.92 g (13.94 mmol) of 85% KOH dissolved in 23 mL of methanol and 2 mL of water is heated at reflux. After maintaining the reaction for 5 h at reflux, it is cooled to 20-25° C. and acidified to pH 7 with HCl 1N. After stirring the suspension for 1 h at 20-25° C., it is filtered with water to provide 1.8 g (82.2%) of N-(4-iodobenzyl)-L-valine. M.p.=256-258° C.

The enantiomeric purity is determined by chiral HPLC, giving e.e.=99.38%

IR (KBr, cm$^{-1}$): 2960, 1610, 1490, 1460, 1410, 1210, 1005, 830.

NMR $^1$H (D$_2$O), sodium salt of N-(4-iodobenzyl)-L-valine, δ (ppm): 0.90 (t, 6H, —CH(C$\underline{H}_3$)$_2$), 1.7-1.9 (m, 1H, —C$\underline{H}$(CH$_3$)$_2$), 2.84 (d, 1H, —C$\underline{H}$—COONa), 3.4-3.8 (dd, 2H, Ar—C$\underline{H}_2$—), 7.15 (d, 2H, ArH), 7.75 (d, 2H, ArH).

(2) To a suspension of 12 g (41.5 mmol) of p-toluenesulphonate of L-valine in 120 mL of CH$_2$Cl$_2$ is added at 20-25° C. and under nitrogen atmosphere 9.6 mL (45.5 mmol) of 1,1,1,3,3,3-hexamethyldisilazane. After shaking the mixture at 20-25° C. for 2 h, 15.9 mL (91.3 mmol) of diisopropylethyl amine and 12.3 g (41.5 mmol) of 4-iodobenzylo bromide are added and heated at reflux. When all the 4-iodobenzylo bromide has been consumed the solvent is evaporated off at low pressure, 120 mL of water is added and after 1 h at 0° C. the solid is filtered and dried in an air oven at 40° C. to provide 11.6 g (84%) of N-(4-iodobenzyl)-L-valine.

The enantiomeric purity is determined by chiral HPLC, giving e.e.=100%

(3) 45.8 mL (0.185 mol) of N,O-bistrimethylsilylacetamide is added under nitrogen atmosphere to a mixture made up of 21.7 g (0.185 mol) of L-valine and 32.3 mL (0.185 mol) of diisopropylethylamine in 12.5 mL of DMF. After 1 h at 80° C. the suspension becomes a clear solution. Then, 50 g (0.168 mol) of 4-iodobenzylo bromide is added in portions at 50° C. and controlling exothermy, and it is left to react at 80° C. for 2 h. The mixture is cooled to 20-25° C., and 250 mL of toluene and a solution made up of 250 mL of water and 80 mL of NaOH 40% is added. The resulting aqueous phase is washed twice with 100 mL of AcOEt, the remains of solvent are distilled and it is taken to pH 6-7 with HCl 3N. The solid obtained is filtered with 250 mL of IPA to give 47.9 g (85.3%) of N-(4-iodobenzyl)-L-valine.

The enantiomeric purity is determined by chiral HPLC, giving e.e.=100%

Example 5

Obtaining N-(4-bromobenzyl)-N-valeryl-L-valine

A mixture made up of 5 g (17.47 mmol) of N-(4-bromobenzyl)-L-valine and 5.9 g (70.24 mmol) of sodium bicarbonate in 50 mL of dry THF is left under stirring and under nitrogen atmosphere for one hour. The preceding suspension is cooled to 0° C. and to it is added over a period of 15 min. 4.2 mL (35.41 mmol) of valeroyl chloride. The mixture is then left to react at 20-25° C. for 3 h, 50 mL of water is added and the THF is distilled at low pressure. The resulting solution is taken to pH 2 with HCl 35% and the remains of THF distilled off completely. The solid obtained is filtered, washed with 50 mL of water and dried in a vacuum over to provide 5.9 g (91.2%) of N-(4-bromobenzyl)-N-valeryl-L-valine. The solid is recrystallised from a mixture of EtOH/H$_2$O 2:1. M.p.=123° C.

The enantiomeric purity is determined by chiral HPLC, giving e.e.>98%

IR (KBr, cm$^{-1}$): 2960, 1720, 1590, 1480, 1420, 1250.

NMR $^1$H (CDCl$_3$), δ (ppm): 0.8-1.1 (m, 9H, —CH(C$\underline{H}_3$)$_2$+—CH$_2$C$\underline{H}_3$), 1.2-1.5 (m, 2H, —C$\underline{H}_2$CH$_3$), 1.5-1.8 (m, 2H, —C$\underline{H}_2$CH$_2$CH$_3$), 2.4 (m, 2H, —CH$_2$CO—), 2.7 (m, 1H, —C$\underline{H}$(CH$_3$)$_2$), 3.7 (d, 1H, —C$\underline{H}$—COOH), 4.3-4.8 (dd, 2H, Ar—CH$_2$—), 7.1 (d, 2H, ArH), 7.5 (d, 2H, ArH).

Example 6

Obtaining N-(4-iodobenzyl)-N-valeryl-L-valine

In a manner analogous to example 5, 11.5 g (91.8%) of N-(4-iodobenzyl)-N-valeryl-L-valine is obtained from 10 g (30.01 mmol) of N-(4-iodobenzyl)-L-valine and 7.12 mL (60.03 mmol) of valeroyl chloride. The solid is recrystallised from a mixture of EtOH/H$_2$O 2:1. M.p.=126-127° C.

The enantiomeric purity is determined by chiral HPLC, giving e.e.>99%

IR (KBr, cm$^{-1}$): 2960, 1725, 1595, 1480, 1405, 1255.

NMR $^1$H (CDCl$_3$), δ (ppm): 0.8-1.1 (m, 9H, —CH(C$\underline{H}_3$)$_2$+—CH$_2$C$\underline{H}_3$), 1.2-1.5 (m, 2H, —C$\underline{H}_2$CH$_3$), 1.5-1.8 (m, 2H, —C$\underline{H}_2$CH$_2$CH$_3$), 2.4 (m, 2H, —CH$_2$CO—), 2.7 (m, 1H, —CH(CH$_3$)$_2$), 3.7 (d, 1H, —CH—COOH), 4.3-4.8 (dd, 2H, Ar—CH$_2$—), 6.9 (d, 2H, ArH), 7.7 (d, 2H, ArH).

Example 7

Obtaining (S)—N-(1-carboxy-2-methyl-prop-1-yl)-N-pentanoyl-N-[2'-(1H-tetrazol-5-yl-)-biphenyl-4-yl methyl]amine (Valsartan)

Homogeneous Catalysis (1) To a mixture made up of 1.35 mL of ethanol, 13.5 mL of 1,2-dimethoxyethane and 4 mL of water are added 0.50 g (1.35 mmol) of N-(4-bromobenzyl)-N-valeryl-L-valine, 0.308 g (1.62 mmol) of 2-(1H-tetrazol-5-yl)phenylboronic acid, 0.156 g (0.135 mmol) of palladium tetrakistriphenylphosphine and 0.324 g (8.1 mmol) of NaOH. The mixture, following scouring with gentle bubbling of nitrogen for 5 min, is heated at reflux for 12 h. The reaction is cooled to 20-25° C. and 25 mL of AcOEt and 25 mL of water are added. The decanted aqueous phase is taken to pH 1-2 with HCl 37% and extracted with 25 mL of AcOEt. After evaporating the AcOEt phase to dryness and purifying by silica gel chromatography (eluent AcOEt/heptane/AcOH 15:5:0.2) 0.356 g (60.5%) of Valsartan is obtained.

NMR $^1$H (CDCl$_3$), δ (ppm): 0.8-1.1 (m, 9H, —CH(CH$_3$)$_2$+—CH$_2$CH$_3$), 1.3-1.5 (m, 2H, —CH$_2$CH$_3$), 1.5-1.8 (m, 2H, —CH$_2$CH$_2$CH$_3$), 2.6 (t, 2H, —CH$_2$CO—), 2.7 (m, 1H, —CH(CH$_3$)$_2$), 3.5 (d, 1H, —CH—COOH), 4.3-5.0 (dd, 2H, Ar—CH$_2$—), 7.0-7.7 (m, 7H, ArH), 8.0-8.1 (d, 1H, ArH in ortho position to the tetrazole ring).

(2) To a mixture made up of 3 mL of methanol, 0.9 mL of water and 0.096 g (2.4 mmol) of NaOH are added 0.250 g (0.60 mmol) of N-(4-iodobenzyl)-N-valeryl-L-valine, 0.137 g (0.72 mmol) of 2-(1H-tetrazol-5-yl)phenylboronic acid and 0.035 g (0.030 mmol) of palladium tetrakistriphenylphosphine. Following scouring with gentle bubbling of nitrogen for 5 min, the mixture is heated at reflux for 2 h. The reaction is cooled to 20-25° C., the methanol is distilled in vacuo and 25 mL of AcOEt and 25 mL of water are added. The decanted aqueous phase is taken to pH 1-2 with HCl 37% and extracted with 25 mL of AcOEt. After evaporating the AcOEt phase to dryness and purifying by silica gel chromatography (eluent AcOEt/heptane/AcOH 15:5:0.2) 0.230 g (88%) of Valsartan is obtained.

(3) Nitrogen is bubbled for 5 min. To a mixture made up of 0.50 g (1.35 mmol) of N-(4-bromobenzyl)-N-valeryl-L-valine, 0.308 g (1.52 mmol) of 2-(1H-tetrazol-5-yl)phenylboronic acid, 0.0028 g (0.016 mmol) of palladium chloride and 0.0084 g (0.032 mmol) of triphenylphosphine in a solution of 2.06 mL (13.0 mmol) of sodium methoxide in methanol al 30% and 5 mL of methanol are added. It is heated at 70° C. under nitrogen atmosphere for 5 h, 0.050 g of activated carbon is added and it is stirred at the same temperature for a further 15 min. After cooling to 20-25° C. it is filtered, the methanol is evaporated and it is treated with 25 mL of HCl 1N and 25 mL of AcOEt. The AcOEt phase is dried with anhydrous sodium sulphate and after distilling the solvent the crude product obtained is purified by silica gel chromatography (eluent AcOEt/heptane/AcOH 15:5:0.2) to provide 0.327 g (55.6%) of Valsartan.

(4) Nitrogen is bubbled for 5 min. To a mixture made up of 0.20 g (0.48 mmol) of N-(4-iodobenzyl)-N-valeryl-L-valine, 0.115 g (0.61 mmol) of 2-(1H-tetrazol-5-yl)phenylboronic acid, 0.017 g (0.024 mmol) of bis(triphenylphosphine)palladium chloride and 0.115 g (2.87 mmol) of NaOH in 2.4 mL of methanol and 0.7 mL of water are added. The reaction is heated to 70° C. under nitrogen atmosphere. Once 3 h has elapsed the reaction is considered to be completed and the methanol is distilled. The crude product is treated with 25 mL of HCl 1N and 25 mL of AcOEt. The AcOEt phase is dried with anhydrous sodium sulphate and after distilling the solvent the crude product obtained is purified by silica gel chromatography (eluent AcOEt/heptane/AcOH 1.5:5:0.2) to provide 0.178 g (85%) of Valsartan.

Heterogeneous Catalysis (5) A mixture made up of 1 g (2.70 mmol) of (4-bromobenzyl)-N-valeryl-L-valine, 0.513 g (2.70 mmol) of 2-(1H-tetrazol-5-yl)phenylboronic acid, 0.120 g of 5% Pd/C in paste (0.028 mmol of palladium) and 0.0084 g (0.032 mmol) of triphenylphosphine in a solution of 4.1 mL (21.5 mmol) of sodium methoxide in 30% methanol and 10 mL of methanol is heated at 70° C. for 10 h. The reaction is cooled to 20-25° C., the catalyst is filtered and the methanol distilled in vacuo. The resulting residue is dissolved in 25 mL of water and, following washing with 25 mL of AcOEt, is acidified to pH 3 with HCl 3N and extracted twice with 20 mL of AcOEt. The combined phases of AcOEt are dried with anhydrous Na$_2$SO$_4$ and following distillation of the solvent the crude product obtained is purified by silica gel chromatography (eluent AcOEt/heptane/AcOH 15:5:0.2) to provide 0.683 g (58%) of Valsartan.

In an analogous way, 0.745 g (71.4%) of Valsartan is obtained from 1 g (2.4 mmol) of N-(4-iodobenzyl)-N-valeryl-L-valine, 0.546 g (2.88 mmol) of 2-(1H-tetrazol-5-yl)phenylboronic acid, 0.120 g of 5% Pd/C in paste (0.028 mmol of palladium) and 0.0074 g (0.028 mmol) of triphenylphosphine in a solution of 3.7 mL (19.4 mmol) of sodium methoxide in methanol at 30% and 10 mL of methanol.

(6) A mixture made up of 0.1 g (0.24 mmol) of N-(4-iodobenzyl)-N-valeryl-L-valine, 0.055 g (0.29 mmol) of 2-(1H-tetrazol-5-yl)phenylboronic acid, 0.038 g (0.95 mmol) of NaOH, 0.0102 g of 5% Pd/C in paste (0.0024 mmol of palladium) and 0.0020 g (0.0035 mmol) of the trisodium salt of 3,3',3''-phosphinidinatris(benzenesulphonate) in 1 mL of water is heated at 70° C. for 2 h. After cooling the mixture to 20-25° C. the catalyst is filtered and 0.1 mL of glacial acetic acid is added to provide, once filtered and dried in an air oven at 45° C., 0.086 g of crude Valsartan. Following purification of this crude product by silica gel chromatography (eluent AcOEt/heptane/AcOH 15:5:0.2) 0.072 g (68%) of Valsartan is obtained.

Purification of the Crude Valsartan

A solution made up of 20 g of crude Valsartan obtained according to example 7 (2) dissolved in 160 mL of AcOEt is treated with 1 g of neutral activated carbon at 45-50° C. for 1 h. The mixture is filtered, and to the clear solution obtained methylcyclohexane is added slowly at 20-25° C. until precipitation, is observed (approximately 120 mL). The mixture thickens at first, and later a fluid suspension is obtained, at which time the slow addition, of a further 120 mL of methylcyclohexane is continued. The mixture is left stirring at 20-25° C. for 3 h, is filtered and dried in a vacuum oven at 45° C. to provide 14 g of Valsartan as a white solid.

La enantiomeric purity is determined by chiral HPLC, giving e.e.>99.5%

The invention claimed is:

1. A process for preparing Valsartan of formula I, coupling an intermediate compound of formula VI with a compound of formula VII:

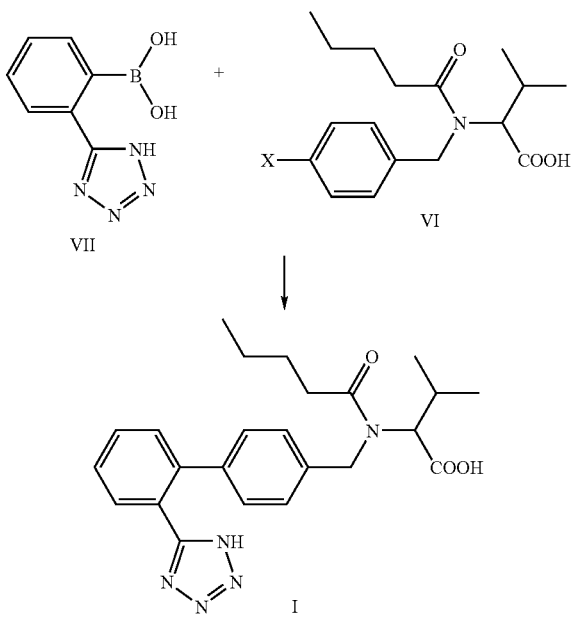

wherein X is a halogen or an —OSO$_2$R group, wherein R is a CF$_3$, a tolyl, a methyl or a F, in the presence of a reaction medium comprising an aqueous solvent, a polar organic solvent or a mixture of water and a water-miscible solvent, an organic or inorganic base able to form a salt with the tetrazole ring, and a catalytic amount of a palladium compound, and at a temperature of between 25° C. and 150° C.

2. The process according to claim 1, characterised in that said coupling is carried out at a temperature of between 50° C. and 100° C.

3. The process according to claim 1, characterised in that said coupling is carried out in homogeneous phase if the palladium compound is soluble in the reaction medium, or in heterogeneous phase if the palladium compound is insoluble in the reaction medium.

4. The process according to claim 1, characterised in that if the palladium compound is soluble in the reaction medium, the palladium compound is Pd(PPh$_3$)$_4$, PdCl$_2$, (PPh$_3$)$_2$, or Pd(AcO)$_2$.

5. The process according to claim 1, characterised in that if the palladium compound is insoluble in the reaction medium, the palladium compound is Pd/C and the coupling is carried out in the presence of a catalytic amount of a phosphine ligand or a phosphine soluble in water.

6. The process according to claim 5, characterised in that said phosphine ligand is a triphenylphosphine.

7. The process according to claim 5, characterised in that said phosphine soluble in water is a trisodium salt of 3,3',3"-phosphinidinatris (benzenesulphonate).

8. The process according to claim 1, characterized in that the compound of formula VI is prepared by N-acylation of a compound of formula (V) with valeroyl chloride:

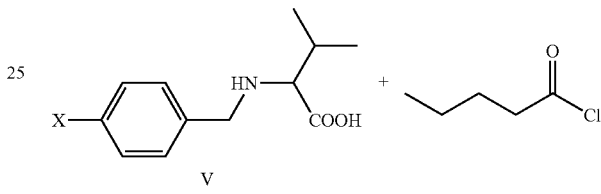

in the presence of an aprotic organic solvent and an organic or inorganic base; and at a temperature of between –20 and 40° C.

9. The process according to claim 8, wherein the aprotic solvent is tetrahydrofurane.

10. The process according to claim 8, wherein the organic base is NaHCO$_3$.

* * * * *